US00PP32836P2

(12) United States Plant Patent
Glawe et al.

(10) Patent No.: US PP32,836 P2
(45) Date of Patent: Feb. 23, 2021

(54) ***PELARGONIUM* PLANT NAMED 'KLEPZ20550'**

(50) Latin Name: *Pelargonium zonale*
Varietal Denomination: KLEPZ20550

(71) Applicant: Klemm+Sohn GmbH & Co. KG, Stuttgart (DE)

(72) Inventors: Martin Glawe, Stuttgart (DE); Nina Neu, Murrhardt (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 16/871,015

(22) Filed: May 10, 2020

(51) Int. Cl.
*A01H 5/02* (2018.01)
*A01H 6/42* (2018.01)

(52) U.S. Cl.
USPC ..... Plt./325
CPC ..... *A01H 6/425* (2018.05)

(58) Field of Classification Search
USPC ..... Plt./325
CPC ..... A01H 6/425; A01H 5/02
See application file for complete search history.

*Primary Examiner* — Keith O. Robinson
(74) *Attorney, Agent, or Firm* — Weatherly IP Solutions, LLC; Barbara Campbell

(57) ABSTRACT

A new *Pelargonium* plant particularly distinguished by pink flowers with red centers, a bushy and mounding habit, and an upright growth habit, is disclosed.

1 Drawing Sheet

Genus and species: *Pelargonium zonale.*
Variety denomination: 'KLEPZ20550'.

BACKGROUND OF THE NEW PLANT

The present invention comprises a new and distinct variety of *Pelargonium*, botanically known as *Pelargonium zonale* and hereinafter referred to by the variety name 'KLEPZ20550'. 'KLEPZ20550' originated from a hand-pollination in July 2012 in Stuttgart, Germany between the female *Pelargonium* variety 'Amri Pikegs', also known as AMERICANA 'Pink Mega Splash' (U.S. Plant Pat. No. 20,481), and the male *Pelargonium* variety 'PZ-2000-Seestern neu' (unpatented).

Seeds from the hand-pollination were obtained. The seeds were sown and plants were grown for evaluation. A single plant was selected in May 2013 and subsequently named 'KLEPZ20550'. In July 2013 'KLEPZ20550' was first vegetatively propagated by vegetative stem cuttings. 'KLEPZ20550' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. Pink flowers with red centers;
2. A bushy and mounding habit; and
3. An upright growth habit.

DESCRIPTION OF THE PHOTOGRAPH

This new *Pelargonium* plant is illustrated by the accompanying photograph which shows an overall view of the plant. The photograph is of an approximately 14-week-old plant grown indoors in Stuttgart, Germany, in February 2020. The colors shown are as true as can be reasonably obtained by conventional photographic procedures.

DESCRIPTION OF THE NEW VARIETY

The following detailed descriptions set forth the distinctive characteristics of 'KLEPZ20550'. The data which define these characteristics were collected from asexual reproductions carried out in Stuttgart, Germany. Data was collected on 7-month-old plants in Stuttgart, Germany under greenhouse conditions in August 2019. Color references are to The R.H.S. Colour Chart of The Royal Horticultural Society of London (R.H.S.), 6$^{th}$ edition (2015).

Classification:
- *Family.*—Geraniaceae.
- *Botanical.*—*Pelargonium zonale.*
- *Common.*—*Pelargonium.*
- *Designation.*—'KLEPZ20550'.

Parentage:
- *Female parent.*—'Amri Pikegs' (U.S. Plant Pat. No. 20,481).
- *Male parent.*—'PZ-2000-Seestern neu' (unpatented).

Plant:
- *Form.*—Bushy and mounding.
- *Habit.*—Upright.
- *Height (from top of soil).*—30.0 cm.
- *Width (horizontal plant diameter).*—44.0 cm.
- *Natural flowering season.*—April to October.
- *Propagation type.*—Vegetative by stem cuttings.
- *Time to produce a finished flowering plant.*—12 weeks.
- *Time to initiate and develop roots.*—4 weeks.
- *Root description.*—Fine, dense, RHS NN155A (White).

Stems:
- *Quantity of stems per plant.*—10.
- *Color.*—RHS 143A.
- *Surface texture.*—Pubescent, sparse.
- *Stem form.*—Round.

*Diameter.*—1.9 cm.
*Length.*—19.0 cm.
*Internode length.*—1.3 cm.
*Anthocyanin.*—Absent.

Leaves:
*Arrangement.*—Alternate.
*Shape.*—Reniform.
*Apex.*—Round.
*Base.*—Wide open.
*Margin.*—Crenate and lobed.
*Depth of sinus.*—2.0 cm.
*Surface texture.*—Upper surface: Pubescent, sparse. Lower surface: Pubescent, sparse.
*Length.*—4.3 cm.
*Width.*—8.3 cm.
*Color.*—Upper surface: RHS 146A (Yellow-green). Lower surface: RHS 146B (Yellow-green).
*Petiole.*—Length: 7.0 cm. Diameter: 0.3 cm. Color: RHS 146C (Yellow-green). Strength: Medium.
*Venation pattern.*—Palmate.
*Venation color.*—Upper surface: RHS 146C (Yellow-green). Lower surface: RHS 146D (Yellow-green).
*Zonation.*—Absent.

Inflorescence:
*Lastingness of flowers on the plant.*—6 to 8 days.
*Flower type.*—Single.
*Umbels.*—Quantity of umbels per plant: 25. Length: 4.1 cm. Diameter: 9.7 cm.
*Individual florets of the umbel.*—Quantity of florets per umbel: 28 to 30. Depth: 1.0 cm. Diameter: 4.2.
*Fragrance.*—Absent.

Flower buds:
*Cluster shape.*—Round.
*Cluster size.*—Length: 1.0 cm. Width: 1.2 cm.
*Surface texture.*—Pubescent, sparse.
*Bud.*—Height: 1.1 cm. Width: 0.6 cm. Shape: Elliptic. Apex: Acute. Base: Obtuse. Margin: Entire. Color: RHS 146C (Yellow-green).

Petals:
*Quantity per flower.*—5.
*Shape.*—Spatulate.
*Apex.*—Round.
*Base.*—Obtuse.
*Margin.*—Entire.
*Length.*—2.5 cm.
*Width.*—2.3 cm.
*Surface texture.*—Upper surface: Smooth. Lower surface: Smooth.
*Color of lobes.*—Upper lobes: Upper surface: The basic color is RHS 73B (a lighter Red-Purple) which is 1.0 cm in width from the margin to the color center and the center is RHS 45B (Red), and is 1.2 cm in width. Lower surface: RHS 73C (light Red-Purple). Lower lobes: Upper surface: The basic color is RHS 73B (a lighter Red-Purple) which is 1.0 cm in width from the margin to the color center and the center is RHS 45B (Red), and is 1.2 cm in width. Lower surface: RHS 73C (light Red-Purple).

Petaloids: Absent.

Sepals:
*Number per flower.*—5.
*Shape.*—Elliptic.
*Apex.*—Acute.
*Base.*—Obtuse.
*Margin.*—Entire.
*Surface texture.*—Upper surface: Pubescent, sparse. Lower surface: Pubescent, sparse.
*Color.*—Upper surface: RHS 146D (Yellow-green). Lower surface: RHS 146D (Yellow-green).
*Length.*—0.7 cm.
*Width.*—0.4 cm.

Pedicel:
*Length.*—2.0 cm.
*Diameter.*—0.2 cm.
*Color.*—RHS 187C (Greyed-purple).
*Surface texture.*—Pubescent, sparse.
*Strength.*—Medium.

Peduncle:
*Length.*—9.4 cm.
*Diameter.*—0.3 cm.
*Color.*—RHS 146B (Yellow-green) at the base and on one side, RHS 184B (Greyed-purple) on the other side.
*Texture.*—Pubescent, sparse.
*Strength.*—Strong.

Reproductive organs:
*Stamens.*—Quantity per flower: 7. Anther length: 0.2 cm. Filament length: 0.5 cm. Filament color: RHS NN155C (White). Pollen amount: Moderate. Pollen color: RHS N30B (Orange-red).
*Pistils.*—Number: 1. Stigma color: RHS 58B (Red-purple). Style length: 0.3 cm. Style color: RHS 58B (Red-purple). Ovary arrangement: Central. Ovary color: RHS 138B (Green). Ovary diameter: 0.2 cm. Ovary length: 0.4 cm.

Fruit and seed set: None observed.

Disease and pest/insect resistance: None observed.

COMPARISON WITH PARENTAL LINE AND KNOWN VARIETY

'KLEPZ20550' is distinguished from its female parent as described in Table 1. No information is available on the male parent.

TABLE 1

Comparison with Parental Line

| Characteristic | 'KLEPZ20550' | Female parent 'Amri Pikegs' |
|---|---|---|
| Vigor | Medium | Compact |
| Size of center/spot in flower | Medium | Big |

'KLEPZ20550' can be compared to the commercial variety 'Swero', also known as PAC 'Flower Fairy Pink' (U.S. Plant Pat. No. 16,752). Differences between the two varieties are described in Table 2:

TABLE 2

Comparison with Similar Variety

| Characteristic | 'KLEPZ20550' | PAC 'Flower Fairy Pink' |
|---|---|---|
| Flower type | Single | Semi-double |

We claim:

1. A new and distinct variety of *Pelargonium* plant named 'KLEPZ20550' as illustrated and described herein.

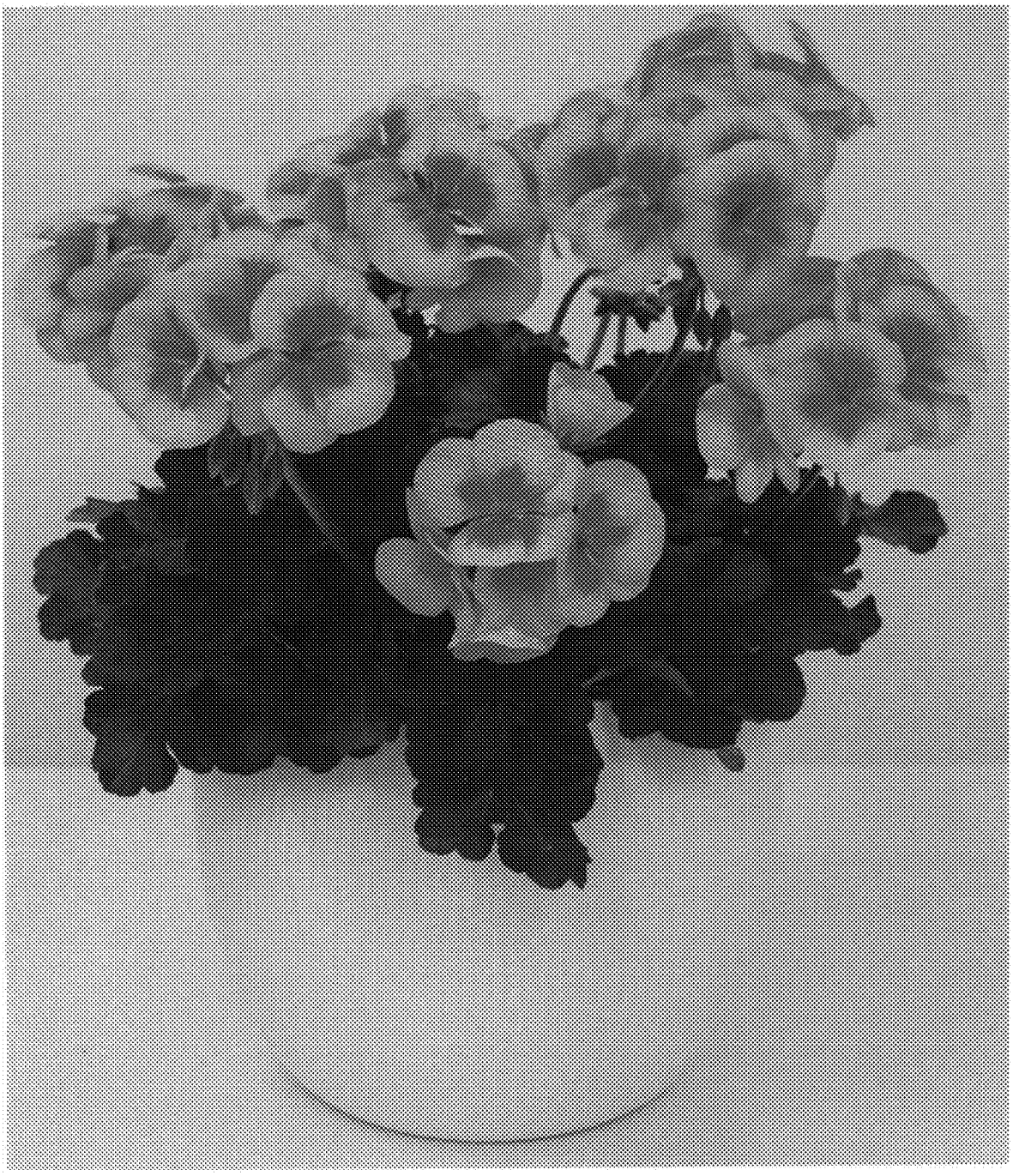

* * * * *